United States Patent [19]

Feldman et al.

[11] Patent Number: 5,265,613

[45] Date of Patent: Nov. 30, 1993

[54] PORTABLE NON-INVASIVE TESTING APPARATUS WITH LOGARITHMIC AMPLIFICATION

[75] Inventors: Yacob Z. Feldman, Willowdale; Isaac Rapoport, Thornhill, both of Canada

[73] Assignee: TelMed, Inc., Miami, Fla.

[21] Appl. No.: 863,184

[22] Filed: Apr. 3, 1992

[51] Int. Cl.$^5$ .................................................. A61B 8/02
[52] U.S. Cl. .................................................. 120/661.07
[58] Field of Search ................ 128/660.07, 661.07, 128/662.04

[56] References Cited

U.S. PATENT DOCUMENTS

| | | | |
|---|---|---|---|
| Re. 28,990 | 10/1976 | Hon et al. | 128/2.06 E |
| 262,571 | 1/1882 | Francis | D24/17 |
| 3,703,168 | 11/1972 | Frink | 128/2.06 R |
| 3,763,851 | 10/1973 | Haff et al. | 128/2.05 Z |
| 3,768,459 | 10/1973 | Cannon et al. | 128/340 |
| 3,780,725 | 12/1973 | Goldberg | 128/2.05 T |
| 3,809,071 | 5/1974 | Davolos et al. | 128/2.06 B |
| 3,813,654 | 5/1974 | Clifton et al. | 340/3 D |
| 3,827,428 | 8/1974 | Hon et al. | 128/2.06 E |
| 3,859,984 | 1/1975 | Langley | 128/2.05 Z |
| 3,934,577 | 1/1976 | Romani | 128/2.05 T |
| 3,989,034 | 11/1976 | Hojaiban | 128/2.06 F |
| 4,086,917 | 5/1978 | Burks et al. | 128/2.05 T |
| 4,157,710 | 6/1979 | Abitbol | 128/642 |
| 4,256,118 | 3/1981 | Nagel | 128/733 |
| 4,281,659 | 8/1981 | Farrar et al. | 128/635 |
| 4,299,234 | 11/1981 | Epstein et al. | 128/698 |
| 4,308,873 | 1/1982 | Maynard | 128/731 |
| 4,403,184 | 9/1983 | Witt et al. | 128/661.07 X |
| 4,413,629 | 11/1983 | Durley, III | 128/660 |
| 4,437,467 | 3/1984 | Helfer et al. | 128/642 |
| 4,493,043 | 1/1985 | Forbath | 364/569 |
| 4,519,396 | 5/1985 | Epstein et al. | 128/698 |
| 4,537,197 | 8/1985 | Hulka et al. | 128/633 |
| 4,573,479 | 3/1986 | Tuccillo | 128/698 |
| 4,642,334 | 2/1987 | Moore et al. | 530/388 |
| 4,738,268 | 4/1988 | Kipnis | 128/775 |
| 4,781,200 | 11/1988 | Baker | 128/670 |
| 4,784,961 | 8/1989 | Russell | 436/63 |
| 4,821,732 | 4/1989 | Lippes | 128/632 |
| 4,860,148 | 4/1987 | Iwamura et al. | 361/58 |
| 4,868,621 | 9/1989 | Miyamoto | 357/23.13 |
| 4,873,986 | 10/1989 | Wallace | 128/670 |
| 4,898,179 | 2/1990 | Sirota | 128/670 |
| 4,925,444 | 5/1990 | Orkin et al. | 604/80 |
| 4,945,917 | 8/1990 | Akselrod et al. | 128/696 |
| 4,951,680 | 8/1990 | Kirk et al. | 128/698 |
| 4,957,109 | 9/1990 | Groeger et al. | 128/640 |
| 4,962,388 | 10/1990 | Quedens et al. | 346/136 |
| 4,984,574 | 1/1991 | Goldberg et al. | 128/653 |
| 4,989,615 | 2/1991 | Hochberg | 128/774 |
| 5,042,499 | 8/1991 | Frank et al. | 128/698 |

Primary Examiner—Francis Jaworski
Attorney, Agent, or Firm—Nath, Lambert & Amberly

[57] ABSTRACT

A portable apparatus for the non-invasive, simultaneous, self-testing of fetal and maternal signals which comprises: a user display means to indicate that the device is operational; an ultrasonic means connected to the device for detecting fetal heart rate; a detection means connected to the device for detecting maternal input signals; signal processing means including a logarithmic amplification means for simultaneously processing fetal heart rate and maternal input signals; and a communication linking mean for the simultaneous transmission of fetal heart rate and maternal input data to a remote output device.

26 Claims, 10 Drawing Sheets

UAmm Hg

FHR bpm

PORTABLE NON-INVASIVE TESTING APPARATUS WITH LOGARITHMIC AMPLIFICATION

BACKGROUND OF THE INVENTION

1. Field of the Invention

The invention relates to a portable apparatus for testing fetal heart rate using ultrasonic means and also simultaneously detecting a maternal input signal. More particularly, the invention relates to the use of a logarithmic amplification means for amplifying the detected fetal heart signal. The invention also relates to the simultaneous transmission of the fetal and maternal input signals to a remote location using communication linking means.

2. Description of Prior Art

In recent years considerable attention has been directed to enhanced methods for fetal and maternal monitoring techniques and procedures. Fetal monitors are widely used to monitor the fetal heart rate as a means for monitoring the fetal condition. In contrast, maternal uterine contractions have been used both during pregnancy and labor, to yield information about the fetus as well as the advancement of labor. Data on these two factors assist the physician to decide whether the condition of the fetus requires immediate medical attention.

Several conventional fetal monitoring systems are routinely used in the care of patients both prior to and during labor and delivery. Fetal heartbeats are routinely detected from the interior abdominal wall indirectly and directly by one of several means. Several indirect methods involve the use of electrodes which pick up the weak fetal electrocardiogram on the maternal abdomen. A sensitive microphone has also been used which picks up fetal heart sounds, or an ultrasonic Doppler transducer can be employed to detect Doppler frequency shifts in ultrasonic energy reflected from moving components of the fetal cardiovascular system. Stethoscopes have also been used to listen to the fetal heartbeat.

The use of stethoscopes for listening to the fetal heartbeat has been unsatisfactory due to the high degree of extraneous or artifact noise which occurs during periods of labor contractions, and such devices are impractical for in-home patient use. Even prior to the commencement of labor, ordinary stethoscopes have been unsatisfactory for use by a physician because the sound of the fetal heart can be masked by the sound of the mother's heartbeat.

Older ultrasonic Doppler systems for monitoring fetal heart rate have been generally inconvenient to use since it was difficult to find the fetal heart beat, and once found the device had to be repositioned frequently. Most of the ultrasonic Doppler systems available to date include an ultrasound probe together with processing circuitry which is attached by wires to a loudspeaker used by the physician. Other known systems which have utilized Doppler probes are hardwired to speakers which, for example, can be clipped to the physician's shirt pocket. Such systems, however, do not appear to have been used by a patient for self-testing purposes, let alone used at home with means enabling separate analyses by a physician.

The heart rate of the fetus has also been monitored with various electronic apparatus to determine certain characteristics of the heart beat. This is usually accomplished by using two electrodes one of which is attached to the head of the fetus. Although this technique has provided reasonably accurate data, there are obvious disadvantages. For example, the electrode cannot be attached to the head of the fetus until the cervix has opened sufficiently and the amniotic sack has been ruptured. For obvious reasons, this technique has not been followed to monitor the fetus in the early stages of labor. In addition, the electrode has been applied either blindly or by means of a special light source which requires special training. Furthermore, the presence of a doctor has been required to supervise the electrode attachment, and is totally impractical for in-home use.

In addition to the foregoing difficulties, the frequent movement of the fetus adds to the problem of deriving reliable signals indicative of fetal heart rate. The problem is intensified even more as a consequence of the multiple sounds generated by the heart valves, in addition to the nonsynchronous impulse noise caused by the fetal and mother movements. Naturally, processing of multiple signals with background noise within a single heartbeat, if processed as consecutive heartbeat signals, would produce a false indication of the fetal heart rate, and therefore provide unreliable instrumentation.

One difficulty associated with these monitoring procedures is that they must be performed in a medically controlled environment, namely in a hospital or doctor's office. Many patients, however, prefer not to leave the comfort and security of their home for the sole purpose of having routine testing procedures performed by a skilled medical professional; yet this preference is counterbalanced by the need for such procedures to be carried out. To date, no effective system has been designed which is capable of monitoring both fetal and maternal input signals in a reliable and safe manner at a site remote from these controlled environments. An in-home testing device would not only benefit the patient but also the medical professional.

The patient is benefitted by avoiding the need to visit the hospital (which is currently the only place where such testing is done) which is time consuming and stressful. This is of particular importance in rural areas where the hospital is far away from the patient's home or is difficult to reach during bad weather conditions. The patient is also benefitted by avoiding costly interruption of work habits if the patient can use a monitoring system in the home setting.

Besides the benefits derived by the patient, the prenatal infant also benefits from in-home testing, first and foremost, since patients may avoid taking this test in the stressful environment created by a hospital setting. A less stressful environment also lowers the risks of premature labor, the risk of creating maternal complications, while also enabling the fetal condition to be diagnosed and tracked at its early stage. In addition, outlying hospitals can transmit ongoing labor data to neonatal centers for expert advice to better diagnose the fetal condition, and a doctor can immediately administer the test during an office examination if he suspects a need for such a test.

With regard to the health care organization, such an in-home monitoring system avoids neonatal care for premature babies, where costs can be astronomical. It further enables earlier detection of fetal complications which can avoid unnecessary problems and expenses while saving hospital bed space for patients who require constant monitoring.

Another notable drawback of conventional fetal monitoring systems is that the detecting sensors must be tightly strapped to the patient in order to obtain adequate signals. This obviously is uncomfortable and inconvenient for the patient, and may result in decreased patient compliance with monitoring schedules.

In view of the noted prior art deficiencies, it would be desirable to have a self-contained system that combines (a) data gathering, (b) data storage, (c) data transmission, and (d) display of data to allow for effective prenatal monitoring.

SUMMARY OF THE INVENTION

The present invention provides an in-home monitoring/testing apparatus that is easily handled by the maternal patient or someone in her presence and can be used to monitor the condition of the fetus by recording maternal input signals and fetal heart rate at a site remote from the user. The invention also provides a means for transmitting the data to a health care practitioner at a remote site, such as a central monitoring facility, by a standard communication linking means, such as a telephone connection.

The present apparatus comprises a lightweight, approximately 3 lbs., recording and transmitting unit. The device is capable of collecting and storing data for up to several hours and preferably up to at least 1.6 hours. The data measured at one convenient location can then be transmitted by the patient user by a standard communications link, with the aid of an autodialer or other suitable means, to a monitoring station located at a remote site.

Due to the wide variations in the signal strength of the detected fetal heart signal, the present invention is based on the discovery that optimum results are obtained when the novel logarithmic amplifier of the invention is used to amplify the detected fetal heart signal.

The portable fetal monitor employs continuous wave Doppler ultrasound to obtain data on fetal heart rate. This preferred method of collection can be achieved with use of a piezoelectric transducer which is placed on the maternal abdomen. A low-power high frequency ultrasound beam is transmitted towards the fetal heart. The echoes returned by fetal cardiac structures are received and electronically processed based on the Doppler shift in frequency due to cardiac movement.

The portable fetal monitor also monitors uterine activity by a tocodynamometer as well as maternal blood pressure using a standard pressure device. A tocotransducer can be conveniently attached to the abdomen in the area of the uterine fundus to measure the relative pressure within the uterus. The device can also be used to monitor maternal heart rate and may be adapted to receive other maternal information such as body weight.

In its broadest aspects, the invention involves a portable testing apparatus for non-invasive simultaneous self-testing of fetal and maternal signals, which comprises: first receiver means for receiving ultrasonic fetal signals; second receiver means for receiving maternal signals; signal processing means including a logarithmic amplification means; first communication means extending between said signal processing means and said first and said second receiver means; and data output means connected to said signal processing means for simultaneous plural signal output and preferably wherein said data output means is also connected to a communication linking means.

As described herein, the present invention provides a portable apparatus for the non-invasive, simultaneous, self-testing of fetal and maternal signals which comprises: a user display means to indicate that the device is operational, an ultrasonic means connected to said device for detecting fetal heart rate, and a detection means connected to said device for detecting a maternal input signal, wherein the device has signal processing means for simultaneously processing fetal heart rate and maternal input signals, said signal processing means including a logarithmic amplification means for amplifying the detected fetal heart signal, and also has a communication linking means for the simultaneous transmission of fetal heart rate and maternal input data to a remote output device.

The device may include means for indicating patient identity as well as means for showing the user the elapsed time of the fetal heart rate and maternal input signal. The ultrasonic means is broadly capable of reading an ultrasonic energy frequency of at least 1 MHz, preferably an ultrasonic energy frequency of about 1 to about 10 MHz, and most preferably an ultrasonic energy frequency of about 2 to about 3 MHz.

In a further embodiment, the ultrasonic detection means is freely positionable by the patient user and may include audible detection means for positioning the ultrasonic detection means to enable maximum measurement of the fetal heart rate. In contrast, the detection means for the maternal input signal is a pressure detection means which can measure uterine activity, maternal blood pressure, or other desirable maternal signal such as maternal heart rate or body weight.

In another embodiment, the device is designed for in-home use and is connected to an output device for reading transmitted data. The device is uniquely connected to an output device which enables the instantaneous viewing of the data as it is being recorded by the user and may include means for the storage of data by either the patient user for later transmission to an output device or storage by the data receiver for subsequent analysis and review by a physician.

In a preferred embodiment, the invention provides a portable apparatus for the non-invasive, simultaneous, self-testing of fetal and maternal signals, which comprises: a user display means to indicate that the device is operational, an ultrasonic means connected to said device for detecting fetal heart rate, a detection means connected to said device for detecting a maternal input signal, said device having signal processing means for simultaneously processing fetal heart rate and maternal input signals, including a logarithmic amplification means for amplifying the fetal heart signal, and said device having a communication linking means for the simultaneous transmission of fetal heart rate and maternal input data to a remote output device, and an output device for reading transmitted data.

In another aspect of the invention, the invention provides a method for monitoring a fetal heart rate and a maternal input signal which comprises: measuring the pressure in the uterus as a function of time, measuring the fetal heart rate using an ultrasonic detection means, simultaneously recording the uterine pressure measurements and the fetal heart rate, and simultaneously transmitting said measurements by communication linking means to a remote location.

Through this method, a device is employed which has a patient identification system, and means for transmitting the data to a remote site for the instantaneous analysis and review of data by a physician. The method also involves a means for storing the data at the patient user site for subsequent transmission by the user and/or storage at the remote site for subsequent analysis and review by the physician.

DETAILED DESCRIPTION OF THE INVENTION

The present invention pertains to a lightweight, portable recording and transmitting unit for simultaneously measuring fetal heart rate and maternal signals. The invention is intended to be used by the patient at her home, where the data can be gathered at her convenience and stored or transmitted to a remote receiving station via a communications link, such as a telephone modem.

The invention contemplates a user display, which indicates when the machine is operational. This user display can also be designed to perform the additional functions of displaying data such as instantaneous fetal heart rate readings and maternal input signal readings. The user display can also provide periodic instructions for operation of the unit, such as to inform the user whether the data has successfully been gathered or transmitted to the receiving station. The user display may also be used to display the elapsed or total recording time for gathering of data.

The present invention employs ultrasound to monitor fetal heart rate, by use of an ultrasound transducer. This can be accomplished with a piezoelectric transducer, placed on the maternal abdomen and connected to the portable unit. A lower-power high frequency ultrasound beam is transmitted towards the fetal heart by the piezoelectric transducer. The echoes returned by the cardiac structures are received and processed electronically to extract on the Doppler shift in frequency due to the cardiac movement.

The detected fetal heart signal varies greatly in strength due to variations in the position of the fetal heart with respect to the ultrasound beam. Therefore, it has been found that a logarithmic amplifier provides optimum results for amplification of the fetal heart signal. Logarithmic amplifiers have been previously used primarily in the field of radar systems, where wide variations in signal strength are common.

Also provided is a means by which proper placement of the ultrasound transducer by the patient may be achieved. This is accomplished by creating an amplified audio signal of the fetal heartbeat, which can be heard by the patient, who can then position the ultrasound transducer so as to obtain the strongest signal The audio signal can be amplified and heard through headphones, a speaker, or in the case of a hearing impaired patient some type of visual indicator to display relative signal strength.

The present invention also measures maternal signals such as uterine activity, or blood pressure or heart rate through a second transducer or other conventional means. Maternal uterine activity or blood pressure signals are usually measured by a pressure transducer, such as a tocodynamometer or a strain gage type transducer which is connected to the portable unit. In the case of measuring uterine activity, this transducer would be attached to the mother's abdomen, usually by means of a cloth belt, in the area of the uterine fundus (just above the navel), where it would measure the relative pressure within the uterus to detect contractions or other activity. It should be understood that the present invention also contemplates the measurement of other maternal signals as requested by the physician such as body weight.

In conjunction with the pressure transducer to measure uterine activity, the present invention contemplates the use of an event marker which can be utilized by the patient to indicate when she actually perceives movement of the fetus or prelabor uterine activity The event marker can be in the form of a hand-held control, which can be connected to the machine to input a signal marking the points in time when the movement is perceived.

The device of the present invention also contains a signal processing means within the portable unit. This generally consists of a digital processing circuit, having a microprocessor with memory for program and data storage, as well as a timer for heart rate calculation and uterine activity (contractions) or blood pressure sampling. The signal processing means also includes a means for logarithmically amplifying the detected fetal heart signal.

The microprocessor is programmed with instructions allowing the unit to initialize its hardware, perform self-tests, initialize the system for operation, set up measurement parameters, sample data, timestamp and store data, calculate and scale rate and pressure data, and collect and transmit data by modem or other communication means. The microprocessor is preferably programmed to transmit information on patient identity and the source of the data being transmitted.

The digital processing circuit also includes sufficient memory storage capacity to store the data gathered during monitoring (while power is supplied), for transmission at a later time if necessary. Preferably, monitoring and data storage are done over several hours and most preferably for up to about 1.6 hours.

The digital processing circuit can also be designed to display, on the user display, rate and pressure data currently being monitored by the unit.

The apparatus of the present invention also includes a transmitting means, within the portable unit, to transmit the data collected on a communications link to a remote output receiving device, such as a monitoring station with a visual screen display, a paper graph generating apparatus, or a memory storage apparatus. This transmitting means would typically be in the form of a telephonic modem.

If the transmitting means is a modem, the modem should ideally be adaptable for tone or pulse phone systems, and for dial-9 systems (a phone system where a trunk access code, such as "9", is necessary to reach an outside line to communicate with lines external to that system). The modem should also be adaptable for dialing long distance. The modem may also have the capability of detecting problems with telecommunication lines, and may be able to refuse or abort data transmission when such problems are detected.

BRIEF DESCRIPTION OF THE DRAWINGS

The present invention will be understood more clearly from the following description of certain preferred embodiments with reference to the associated drawings.

DETAILED DESCRIPTION OF CERTAIN PREFERRED EMBODIMENTS

Figure 1:
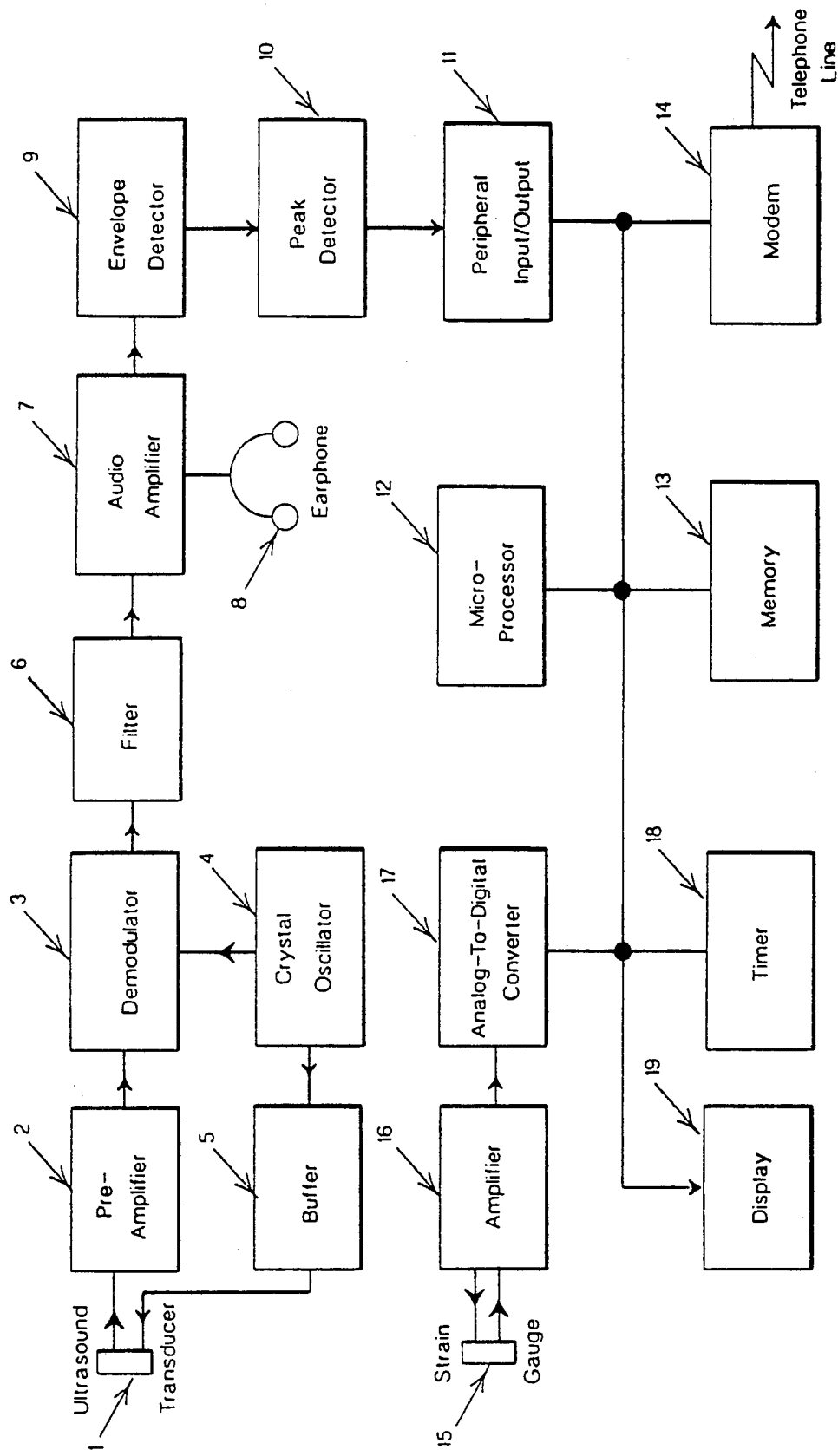
FIG. 1 is a block diagram of the apparatus for simultaneously measuring fetal heart rate and uterine activity.

FIG. 1 illustrates in block diagram form, one preferred embodiment of an apparatus for simultaneously measuring fetal heart rate and maternal uterine activity in accordance with the present invention. The apparatus includes two transducers: ultrasound transducer 1, which detects the fetal heart rate, and strain gage 15, which acts as a pressure transducer to detect relative pressure changes of the mother's uterus. Both transducers are placed directly on the mother's abdomen to obtain readings.

In an alternative preferred embodiment, a blood pressure transducer or other known transducer may be employed in place of strain gage 15, to monitor maternal blood pressure or other maternal signals. The actual type of transducer used would depend on the type of signal being measured.

Ultrasound transducer 1 is excited by a signal produced by oscillator 4, such as a 2 MHz oscillator, passed through buffer 5. The returned ultrasound echoes received by transducer 1 are amplified by low-noise logarithmic preamplifier 2, to increase the signal to noise (S/N) ratio. The signal is then passed through demodulator 3, which eliminates the carrier frequency from the signal. The signal is then passed through filter 6, which has a pass band in the range of 100–600 Hz. The resulting baseband frequencies remaining in the signal are then amplified by amplifier 7.

Audio amplifier 7 produces an audible fetal heart rate signal which when passed through earphones 8, can be heard by the mother. The mother can then listen to this audible signal, and use it to properly place ultrasound transducer 1 on an area of her abdomen that maximizes the strength of the signal, based on the volume changes that she hears.

After the signal passes through amplifier 7, it is passed through envelope detector 9, and peak detector 10, which measure the audio peaks of the signal. Envelope peaks in the signal, as detected by envelope detector 9 and peak detector 10, are then timestamped by microprocessor 12, by means of timer 18 and peripheral input/output means 11, to generate interrupts to the processor. This process has the effect of measuring the fetal heart rate signal.

Uterine activity is measured with a pressure transducer, such as strain gage 15. Strain gage 15, produces a voltage signal in response to relative pressure changes of the uterus, such as those occurring during labor contractions. The signal produced by strain gage 15, is then passed through amplifier 16, having a high gain, high common mode rejection ratio, which is capable of amplifying a low frequency voltage signal. The signal is then passed through a 14 bit analog to digital converter 17, so that the resulting digitized signal can be read by microprocessor 12.

A preferred embodiment of the apparatus of the present invention includes a digital processing circuit consisting of microprocessor 12, having memory capability 13, for program and data storage as well as a timer for heart rate calculation and contraction sampling. The fetal heart rate signal is typically sampled at a rate in the range of 4–10 times per second, most preferably 8 times per second. The uterine pressure signal is typically sampled at a rate in the range of 1–4 times per second, most preferably 2 times per second. The memory 13 is capable of storing all data collected during the sampling period while power is supplied to the apparatus. Once power is turned off, however, the memory is preferably cleared. Alternatively, the data can be permanently stored, with the apparatus having means for clearing memory available to the patient user or physician reader.

A display 19, such as a liquid crystal digital (LCD) display, is connected to the microprocessor and is used for parameter set-up and continuous display of fetal heart rate and maternal input data. This enables the patient user to determine that the apparatus is functioning properly. Display 19 can also display the current time as measured by standard digital timer 18.

Modem 14 allows data stored in memory 13 during monitoring to be sent by standard communication linking means to a remote output device such as a computer, a video monitor, or a graphic plotter such as a paper chart plotter.

Figure 2:
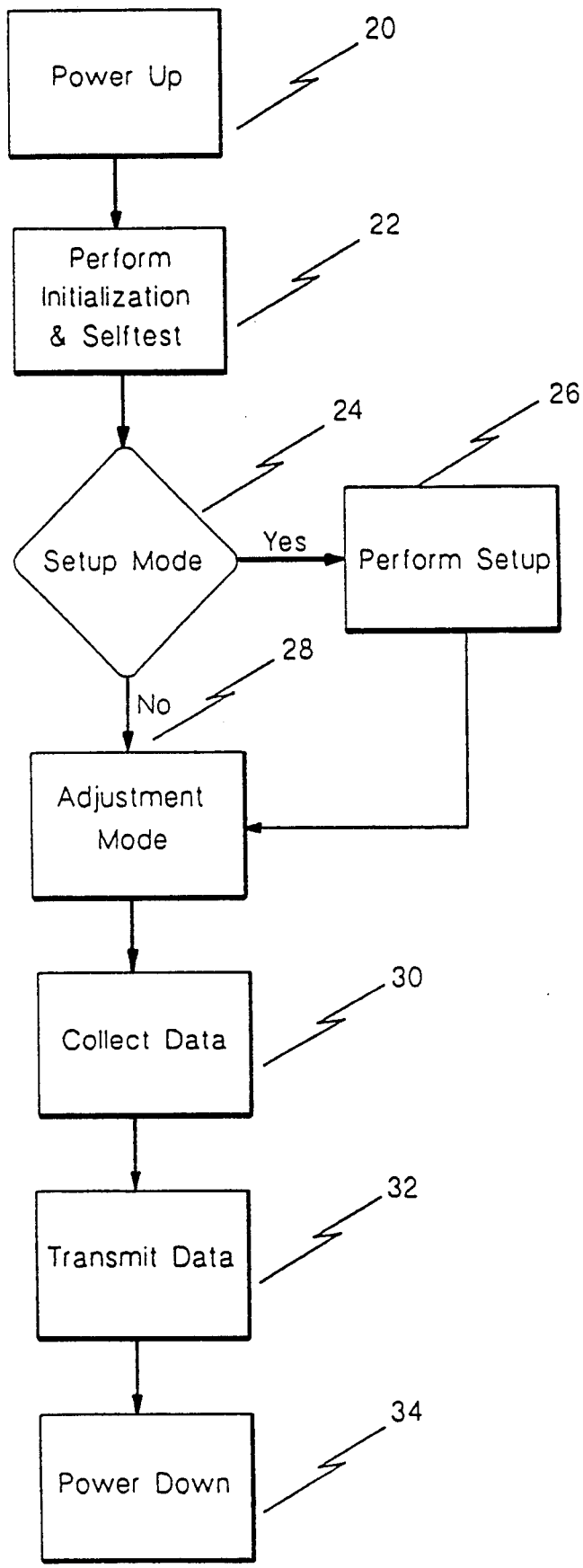
FIG. 2 is a logic flowchart illustrating the operation of an apparatus for simultaneously measuring fetal heart rate and uterine activity to gather and transmit data.

The system depicted in FIG. 1 is controlled by a number of programs stored in memory 13 to drive microprocessor 12. FIG. 2 is a logic flowchart illustrating the sequence of programs which control the operation of the apparatus.

Figure 3:
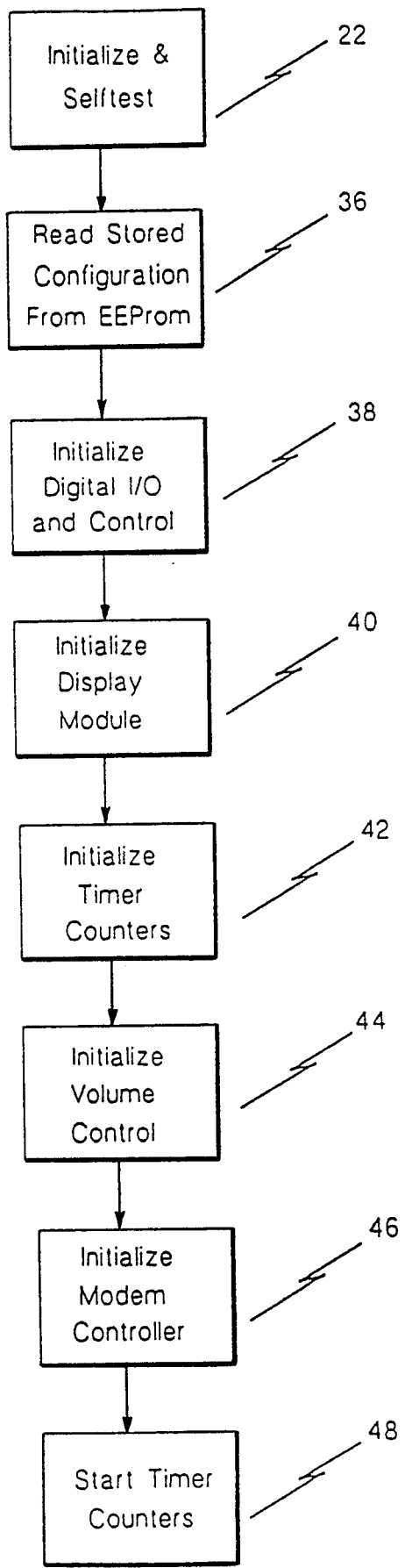
FIG. 3 is a logic flowchart illustrating the initialization and self-test process, depicted in FIG. 2.

As illustrated in FIG. 2, microprocessor 12 of FIG. 1 is programmed to perform the following steps after the apparatus is turned on by connection to a power supply. After turned on by power up step 20, the apparatus goes through an initialization and self-test step 22, which is more fully illustrated in FIG. 3.

After this, the apparatus enters setup mode step 24 at which time certain parameters such as identification codes, modem dialing information and test parameters may be entered into memory 13. At this point, the patient user has a choice of running the entire setup mode routine illustrated in FIG. 4, if new parameters are to be entered, or proceeding directly to adjustment mode step 28.

Figure 5:
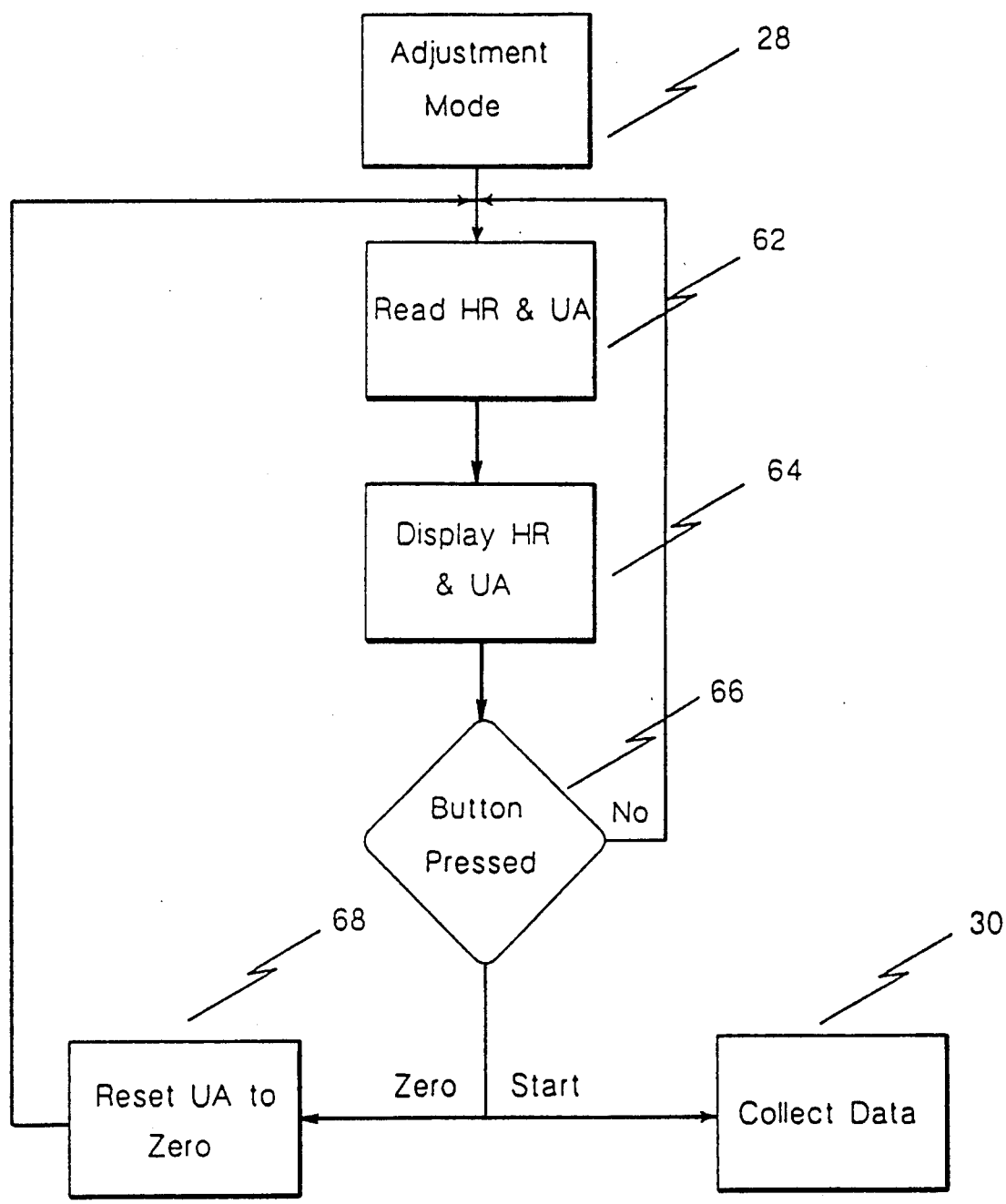
FIG. 5 is a logic flowchart illustrating the adjustment procedure illustrated in FIG. 2.
Figure 6:
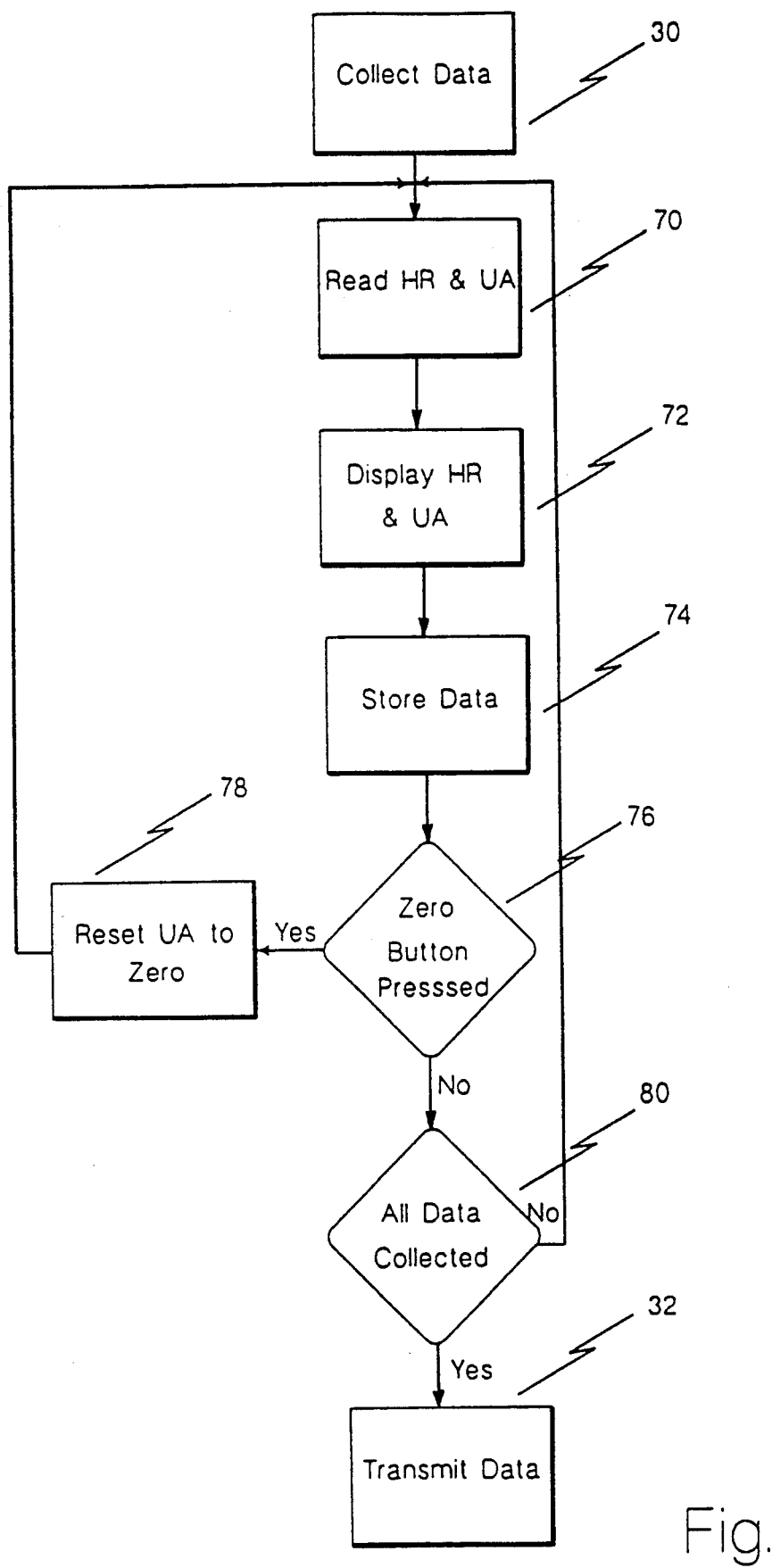
FIG. 6 is a logic flowchart illustrating the data collection procedure depicted in FIG. 2.
Figure 7:
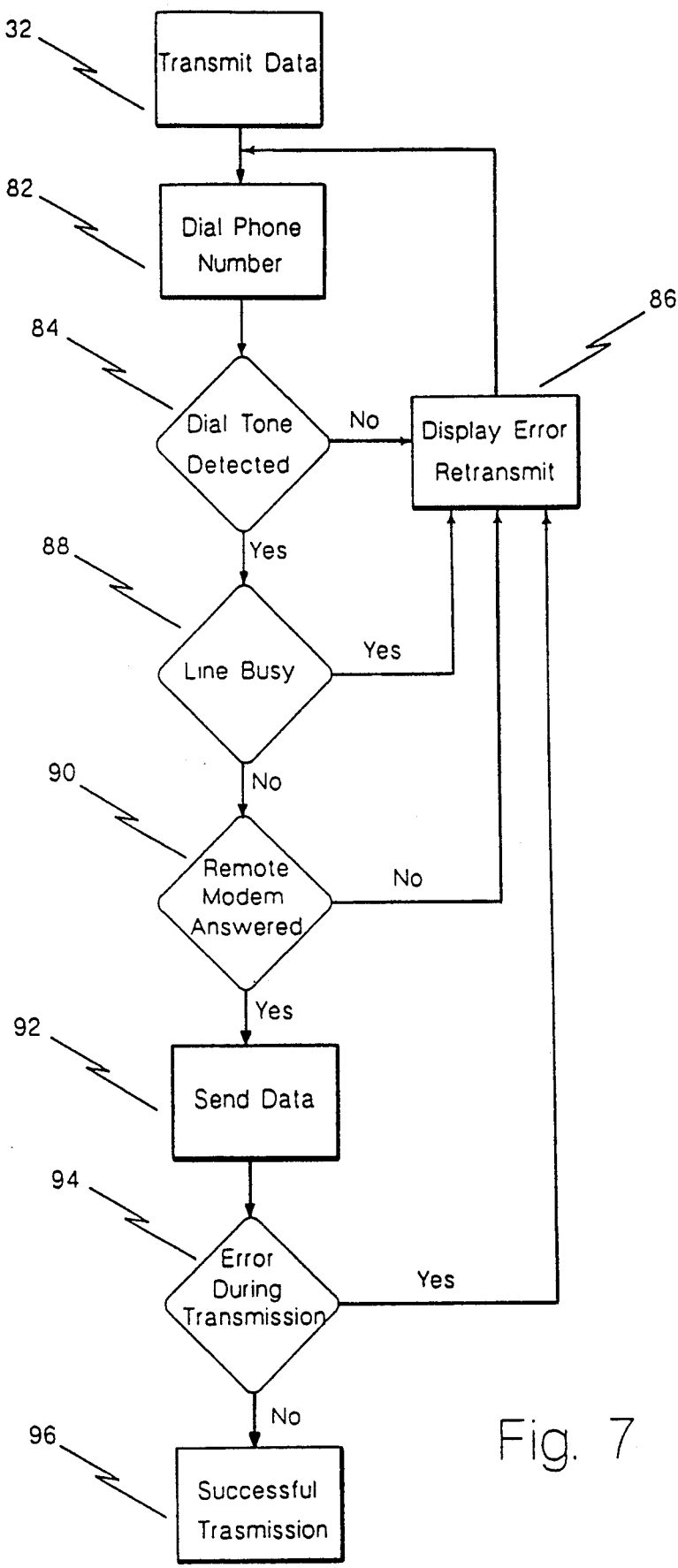
FIG. 7 is a logic flowchart illustrating the data transmitting procedure depicted in FIG. 2.

During adjustment mode step 28, which is fully illustrated in FIG. 5, the apparatus measures and displays values for fetal heart rate and uterine activity, allowing for review of these values. The apparatus remains in adjustment mode step 28 until it receives a signal to proceed to collect data step 29. The collect data routine is fully illustrated in FIG. 6. Once all data is collected, the apparatus proceeds to the transmit data step 32. The full transmit data routine is illustrated in FIG. 7. After the transmit data step 32, the apparatus is turned off by disconnecting the power supply in power down stage step 34.

FIGS. 3 through 7 more fully describe the programmed routines performed by the apparatus during operation. After power up step 20, the apparatus performs the initialization and self-test procedures illustrated in FIG. 3.

First, microprocessor 12 reads the stored configuration from its memory which is typically on the EEProm step 36. An EEProm is an acronym for "Electrically Erasable Programmable Read Only Memory". The EEProm is an erasable, programmable memory chip which is programmed to store a configuration containing initializing instructions for activating the hardware circuitry of the apparatus with preprogrammed initial values. This stored configuration is used to complete the remaining steps of the initialization and self-test procedure, namely: initializing the digital input/output 11 and control step 38, initializing display module 19 step 40, initializing the timer counters in microprocessor 12, peripheral input/output 11, and analog to digital converter 17 step 42, initializing the volume control for audio amplifier 7 step 44, and initializing modem controller 14 step 46.

After all of the hardware has been initialized by providing the necessary starting values read from the configuration stored in the EEProm, the various timer counters within microprocessor 12, peripheral input/output 11 and analog to digital converter 17, are started at step 48.

After the initializing and self-test procedure 22, the apparatus is directed to begin setup mode 24. At this point, the program provides the patient user with an alternative choice as to whether setup 26 is to be performed or whether the apparatus should proceed to adjustment mode 28.

Figure 4:
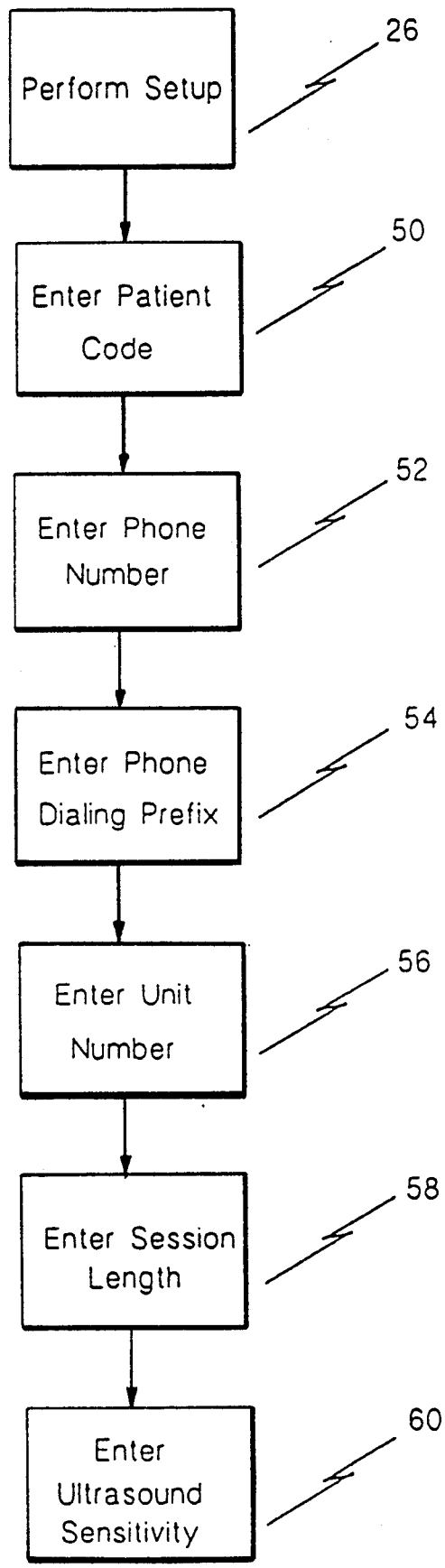
FIG. 4 is a logic flowchart illustrating the setup procedure depicted in FIG. 2.

If setup 26 is chosen the routine illustrated in FIG. 4 is followed. The perform setup 26 routine requests input information from the user in the following manner: patient code step 50 which can request an identifying code for the patient to identify the origin of the collected data; enter phone number step 52 requests the phone number of the receiving station for the data to be transmitted; enter phone dialing prefix step 54 requests the dialing prefix for the phone number of the receiving station for the data to be transmitted, such as long distance prefix, or any information necessary for a dial-9 system, such as a trunk code or extension number; enter unit number step 56 requests the identification number for the particular apparatus that will be transmitting the data; enter session length step 58 requests the total sampling time period for which data will be collected; and enter ultrasound sensitivity step 60 requests information on the amplification level which will be used with the apparatus.

The parameters named in the perform setup routine 26, do not necessarily have to be entered in any particular order. FIG. 4 illustrates one possible order as an example of a preferred embodiment. Also, other parameters may be entered during setup in addition to or in substitution for those listed, memory permitting.

Setup 26 would typically be done by the physician or hospital staff who would be receiving the monitoring information before the apparatus is given to the patient. In a preferred embodiment, the person performing the setup procedure would enter data from a computer, responding to input prompts given by user display 19 of the apparatus. The information entered would then be stored in memory 13 of FIG. 1 of the apparatus.

If the operator chooses to bypass setup 26 while in setup mode 24, or upon completion of setup 26, the program directs the apparatus to begin adjustment mode 28. Adjustment mode 28 is fully illustrated in FIG. 5.

In adjustment mode 28, the apparatus is directed to read the fetal heart rate and uterine activity step 62, and display the readings on user display step 64. At this point, the apparatus checks for a signal from the user for its next instruction, button pressed step 66. The apparatus has a control panel shown in FIG. 9 having user display 19, send button 33 and start button 31. Send button 33 is used to set the initial pressure reading from the strain gage 15 to zero. Start button 31 is used to begin collecting heart rate and pressure data to be stored and transmitted. During step 66, the patient user has the option of pressing the send button, pressing the start button or not pressing any button.

If the user chooses not to press any button, no signal is received by the apparatus, and the program directs the apparatus to go back to step 62 to take another heart rate and uterine activity reading, display the reading step 64, and check for a signal step 66. This cycle will continue until a signal is received as a result of the use pushing a button at step 66.

If during step 66, the user pushes send button 33, the program proceeds to step 68, and the value for uterine activity as measured by strain gage 15 of FIG. 1 will be set to zero. Because the strain gage measures relative pressure changes within the uterus, step 68 is necessary to obtain a zero reference point from which uterine pressure can be measured. In the preferred embodiment as shown in FIG. 1, strain gage 15 is held in place on the mother's abdomen by cloth belt 21. The pressure from the belt 21 will cause strain gage 15 to read some arbitrary value. The reset procedure of step 68 removes the pressure value attributable to belt 21, so that a more accurate relative pressure reading can be obtained.

After the uterine activity value is set to zero in step 68, the program directs the apparatus to return to step 62 to take another heart rate and uterine activity measurement. The reading is then displayed at step 64, and the program proceeds to step 66.

Figure 9:
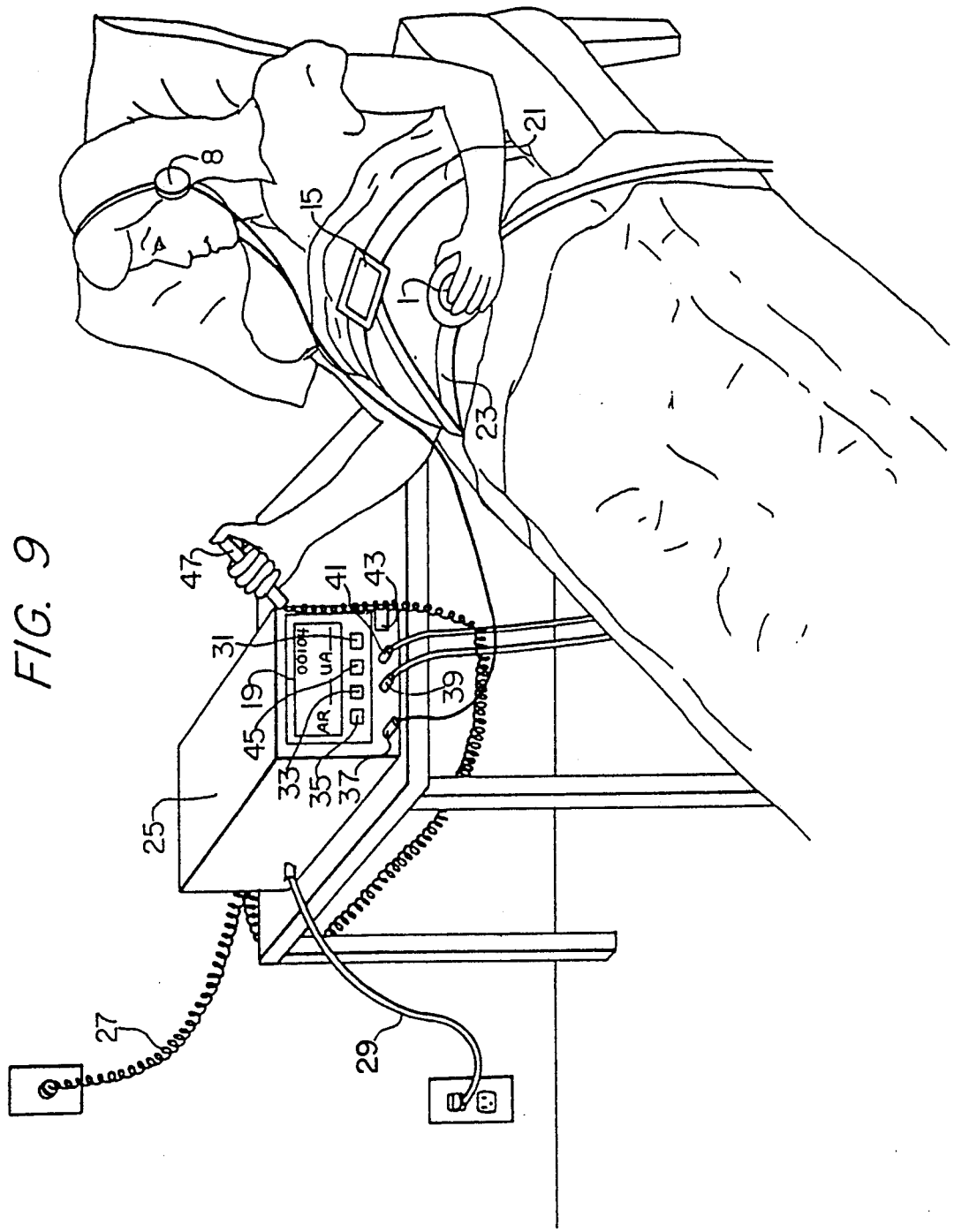
FIG. 9 illustrates the use of an apparatus according to the diagram of FIG. including positioning of the transducers and a preferred embodiment of the patient use control panel.

In the preferred embodiment, during the adjustment mode 28, the user can also use the heart rate display step 64 to determine the proper placement of ultrasound transducer 1 as shown in FIG. 9. By moving transducer 1, the user can observe fluctuations in the fetal heart rate measurement, and find the location where the signal is strongest, thus optimizing the operation of the apparatus. The patient user can also use earphones 8 at this time, to determine the strength of the fetal heart rate signal by means of the volume of the signal.

If the user presses start button 31 during step 66, the program directs the apparatus to proceed to collect data step 30.

The collect data step 30 program directs the apparatus to read the heart rate and uterine activity values at step 70, display the heart rate and uterine activity values at step 72 on user display 19 of FIG. 9, and store the data at step 74 in the memory 13 of FIG. 1. At this point, the program requires a decision, and directs the apparatus to check for a signal resulting from send button 33 of FIG. 9 being pressed by the patient user at step 76.

If signal is received during step 76 that a send button 33 has been pressed, the program proceeds to step 78 which resets the value for the uterine activity reading to zero, then directs the apparatus to return to step 70 to take another fetal heart rate and uterine activity reading, and to cycle through steps 72 and 74 until reaching step 76 again.

If no signal is received during step 76, the program proceeds to step 80 which requires a decision as to whether all data has been collected. To determine whether all data has been collected, the microprocessor 12 of FIG. 1 performs a comparison between the total sampling time, (which is preprogrammed during setup step 26 as the session length step 58 input and stored in memory 13), and the total elapsed sampling time as measured by microprocessor 12.

If during step 80, the elapsed sampling time is less than the total sampling time, microprocessor 12 determines that all data is not collected at step 80, and the program instructs the apparatus to return to step 70 to take another fetal heart rate and uterine activity reading, and to continue through steps 72, 74 and 76, eventually returning to step 80.

If during step 80, the elapsed sampling time is equal to or greater than the total sampling time, microprocessor 12 determines that all data has been collected, and the program proceeds to transmit data step 32.

In another preferred embodiment, the transmit data step 32 would begin in response to a signal from the patient user pushing send button 45 of FIG. 9. The program would direct the apparatus to store the data in memory 13 of FIG. 1 until the apparatus perceives a signal to transmit data at step 32, or until power is disconnected from the apparatus.

In another preferred embodiment, the transmit data program step 32 directs microprocessor 12 of FIG. i to drive modem 14 to dial the phone number step 82 of the remote modem at the receiving station to establish a communications link so that the data can be telephonically transmitted. After dialing the number, the program reaches a decision block step 84, which directs the modem 14 to determine whether a dial tone is detected in response to the dialed number.

If no dial tone is detected in step 84, the microprocessor is directed to display the error message "Error Re-transmit" step 86 on user display 19 of FIG. 1, and then to return to step 82 to dial the phone number of the remote modem.

If a dial tone is detected by modem 14 of FIG. 1 in step 84, the program reaches another decision block step 88, which directs modem 14 to determine whether the line to the remote modem is busy. If modem 14 detects that the line is busy, the program goes back to step 86, displaying the error message "Error Re-transmit" on user display 19 of FIG. 1, and then goes to step 82 to dial the phone number of the remote modem.

If during step 88 modem 14 determines that the line to the remote modem is not busy, the program proceeds to a third decision block step 90, which directs modem 14 to determine whether the remote modem has answered the call to establish a communications link. If modem 14 determines that the remote modem did not answer, the program goes back to step 86, displaying the error message "Error Re-transmit" on user display 19, and then goes to step 82 to dial the phone number of the remote modem.

If during step 90, modem 14 determines that the remote modem did answer, the program directs modem 14 to send data at step 92 to the remote modem. After send data step 92, the program reaches the fourth decision block, step 94, which directs modem 14 to determine whether any errors occurred during the transmission of data. If modem 14 determines that an error in data transmission did occur, the program goes back to step 86, displaying the error message "Error Re-transmit" on user display 19, and then goes to step 82 to dial the phone number of the remote modem.

If during step 94 modem 14 determines that there was no error in transmission of data, the program proceeds to step 96 successful transmission. After step 96, the program is directed to step 34 power down, at which point the power supply is disconnected.

Figure 8B:
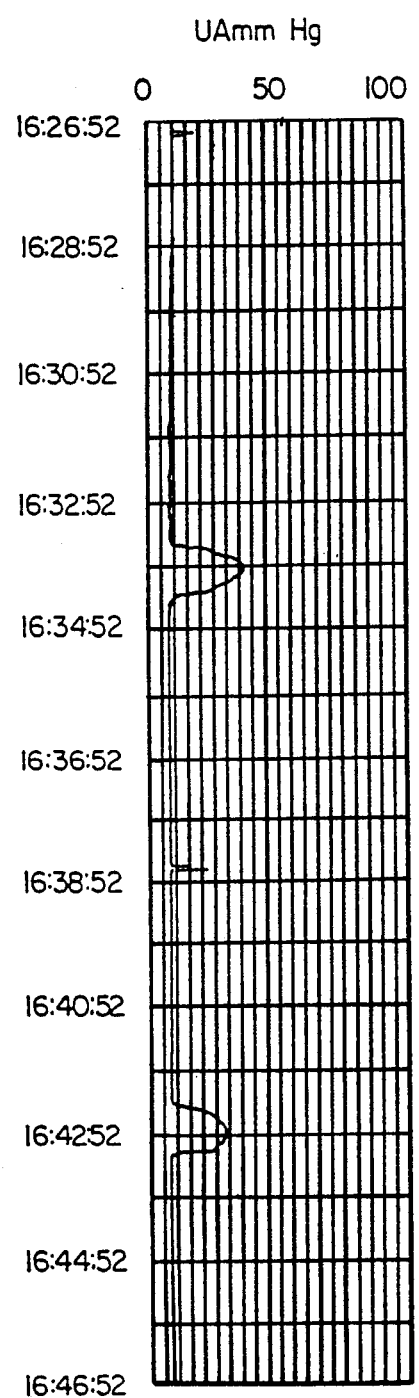
FIGS. 8A and 8B are waveform diagrams illustrating one possible measurement of fetal heart rate in FIG. 8A, and the corresponding simultaneous measurement of maternal uterine contractions in FIG. 8B, obtained from use of an apparatus as depicted diagrammatically in FIG. 1.
Figure 8A:
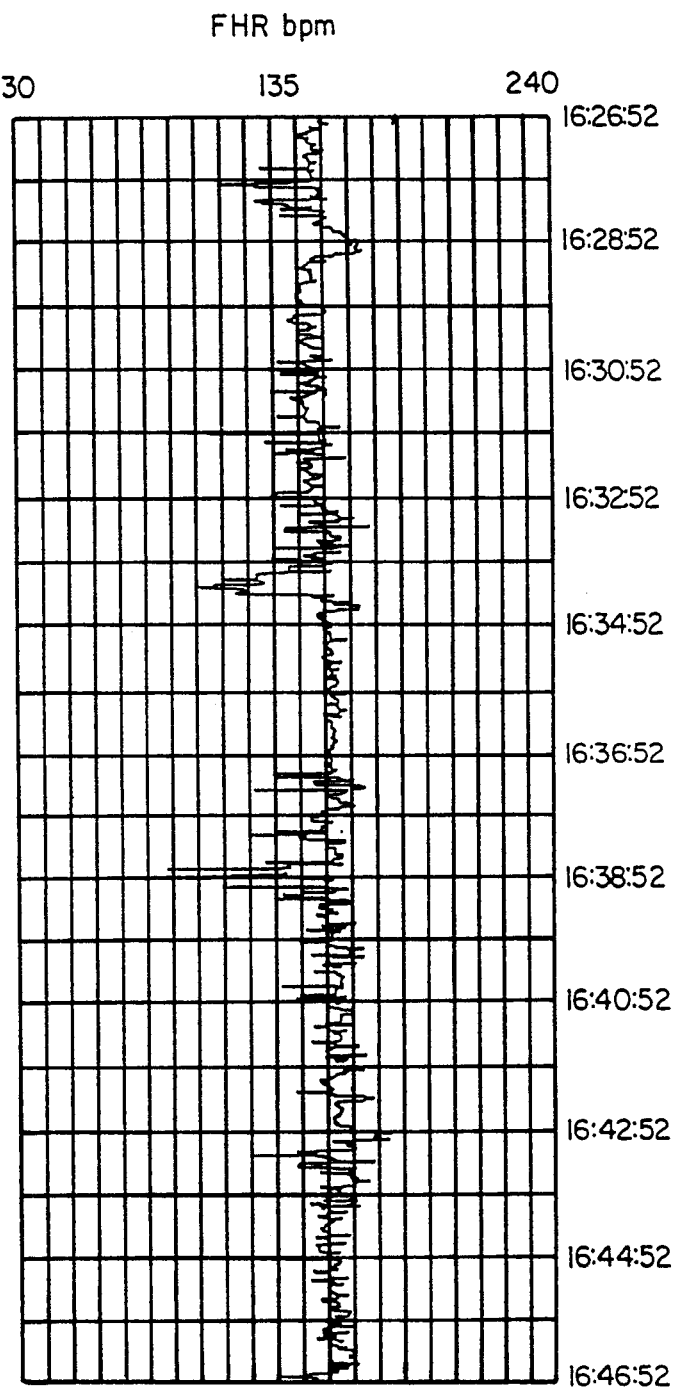

A sample output measurement in the form of a waveform diagram is illustrated in FIGS. 8A and 8B. FIG. 8A shows a typical fetal heart rate signal (unedited) as measured by a continuous wave Doppler type ultrasound transducer. FIG. 8B shows a typical uterine contraction signal as measured by a pressure transducer, such as a strain gage.

Also, in another preferred embodiment, the apparatus is equipped with event marker 47 of FIG. 9, typically in the form of a hand held control. Event marker 47 is connected to the apparatus so that it can send an interrupt signal to microprocessor 12 of FIG. 1 that is stored in memory 13 with the data. The event marker 47 is pressed by the mother whenever she perceives movement of the fetus or a contraction of her uterus. The apparatus emits an audible "beep" each time event marker 47 is pressed to let the mother know that the interrupt has been received and recorded by the apparatus. This interrupt signal appears typically as a line marked on the output waveform (see FIGS. 8A & 8B) when the data is read at the receiving station, to provide an additional indicator to the physician to assist in reading the output data and forming a diagnosis.

In a preferred embodiment as depicted on FIG. 9, the apparatus is designed to meet the following specifications:

The apparatus should be designed to plug into an ordinary residential power outlet, operating on 110-120 V, most preferably at 117 V, 60 Hz cycle alternating current, and a maximum of 40 Watts of power. The power connection can be made using standard power cable 29, such as those used for a computer. The maximum amount of current leakage should be less than 10 microamperes. The operating temperature should be in the range of 0° to 50° C.

The connection to the phone lines is made with a modular plug or adaptor 27, one end of which is plugged directly into a home telephone outlet, the other end plugging into the rear panel of the apparatus to connect to modem 14 of FIG. 1.

Modem 14 should be Bell 103 compatible, and have a data transmit time of at least 2 minutes.

Memory 13 should have an ample data storage capacity which may vary widely depending on the amount of data to be transmitted and most preferably of 99 minutes, 99 seconds worth of recorded fetal heart rate and uterine activity data.

The ultrasound transducer 1 may be a continuous wave Doppler type, such as those currently manufactured by Hewlett-Packard or Corometrics. The dynamic range of the instrument should be around 40 dB, with an input sensitivity of less than 10 millivolts. The transmitter frequency used to excite the ultrasound transducer 1 should be approximately 2.3 MHz, with a transmitter power of less than 10 milliwatts/cm$^2$. The ultrasound transducer 1 should be capable of detecting a heart rate range of at least 30-240 beats per minute. The computations performed to determine the heart rate use a digital, peak detecting, event-to-event method, with a resolution of 1 beat per minute (bpm).

It is anticipated that the detected fetal heart signal strength will primarily lie in a wide range, for example from 10 millivolts to 1.5 volts but is generally from of about −45 dBm to +2 dBm. Occasionally, the detected fetal heart signal may be as low as −70 dBm and possibly as high as +5 dBm. These signal strength values are in relation to a one milliwatt signal which is referred to as 0 dBm. A signal at −70 dBm is therefore 70 dB lower than a one milliwatt signal.

This wide variation is due to the inconsistent angular relation between the fetal heart and the ultrasonic beam. Therefore it has been found that the use of a logarithmic amplifier provides optimum results for providing the amplification of a signal with such a wide dynamic range. Logarithmic amplifiers have found prior applications in other receiver systems, primarily in the field of radar systems.

The logarithmic amplifier provided in the apparatus of the invention has been found to enhance the performance of the fetal monitor by minimizing carrier leakage and amplitude smoothing by decreasing peak S/N. In addition it minimizes the negative effects of amplitude variation which commonly occur during the measurement of fetal heart rates. Also, the logarithmic amplifier enables an acceptable signal to be measured with a reduced tightness of the straps used to hold the sensors in place. This results in enhanced patient comfort and safety during the fetal monitoring process, and improves patient compliance with self-monitoring routines.

Figure 10:
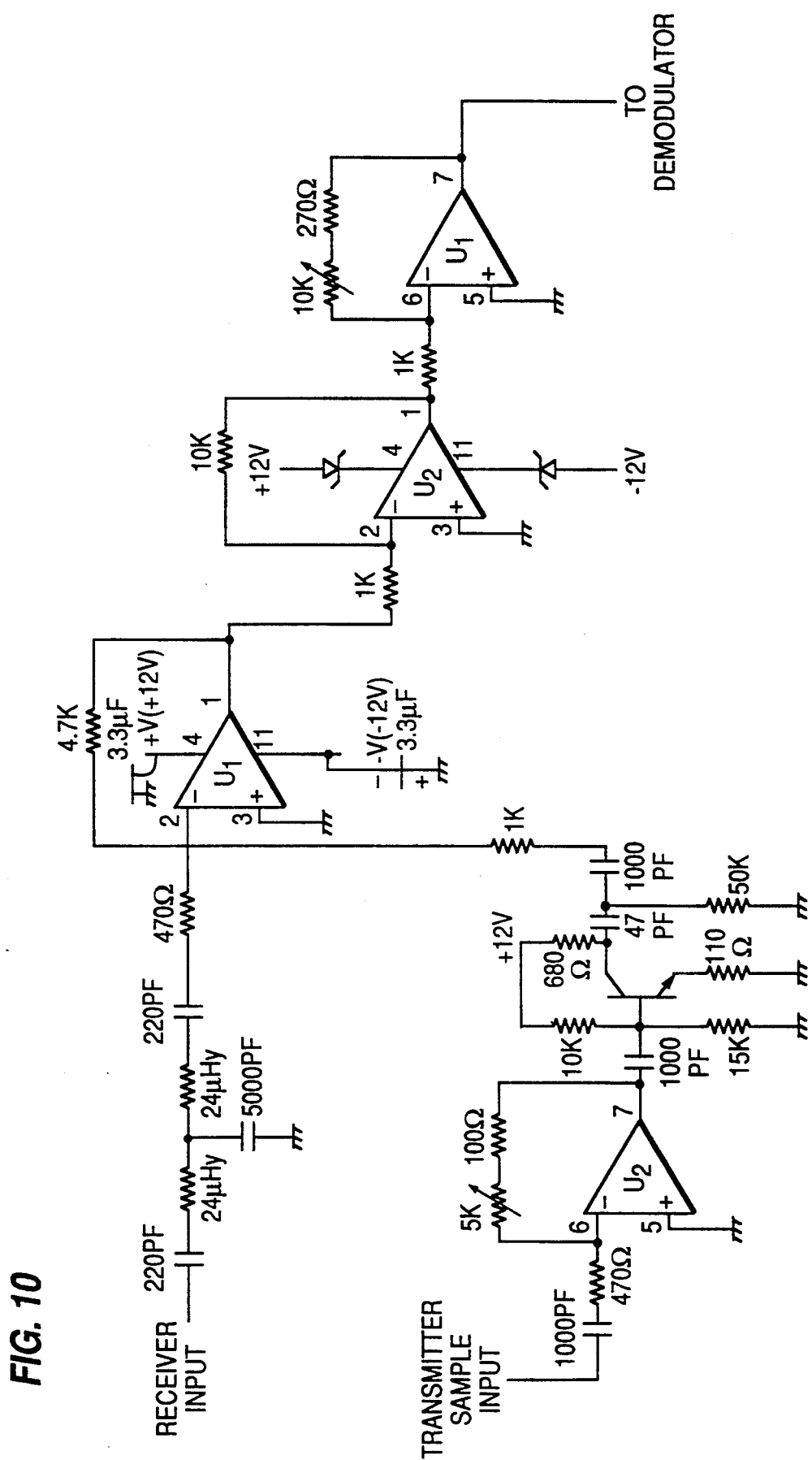
FIG. 10 illustrates the preferred logarithmic amplifier circuit of the invention for amplifying the fetal heart signal.

FIG. 10 illustrates a typical logarithmic amplifier. The circuit includes amplification stages U1A, U1B, U2A, U2B, as well as resistors R1, R2, R11, R12, R13, R14 and P2 which determine the gain of each stage.

The amplification stages are operational amplifiers using operational amplifiers LM 837s. In this regard, U1 and U2 are LM 837 amplifier, such as are manufactured by National Semiconductor Company, USA.

The reason for using this operational amplifier is that it can be used to achieve a logarithmic curve. At low frequency the amplifier will behave as a linear amplifier.

Capacitors C1, C2, C3, and inductors L1 and L2 are used for filtering the input signal.

U2A and transistor Q1 are used for sampling the transmitter signal inverting it for canceling the unwanted transmitter leakage to the receiver input Transistors conventionally used in the art are used herein, such as 2N2222 transistors.

Other components used are C6, C7, C8, C9, R3, R4, R5, R6, R7, R8, R9, R10 and P1.

Z1 and Z2 are used to provide a proper voltage for U2.

It should be recognized that this is but one design for the logarithmic amplification stage and that other designs for the logarithmic amplifier are possible according to the invention. The following table sets forth the values of the individual logarithmic amplifier components which are found in the preferred embodiment:

The pressure transducer or strain gage 15, may be a tocodynamometer type transducer, such as those manufactured by Hewlett-Packard or Corometrics. The tocodynamometer should have a sensitivity of at least 25 u/cm, a linearity of about 1%, a range of at least 0-120 gm or 0-100 μ, a resolution of 1 mm Hg, zero adjust capability (accomplished in the preferred embodiment by pressing the send button on the control panel of the apparatus), a zero accuracy of ±1 mm Hg, a bandwidth of at least 0-1 Hz, a differential input impedance of >1 Megohm, and a common mode input impedance of >10 Megohms.

Earphones 8 can be any mono earphones generally available at electronics or department stores.

The remote output device should be a monitoring system, preferably with an IBM-AT or compatible personal computer unit with at least 640k RAM, one floppy disk (any size), one hard disk (size dependant on number of patients to be monitored, MS-DOS 3.1 or higher, having a 2400 Baud internal modem and an IBM compatible dot matrix printer).

The monitoring station should also have a device capable of producing a paper chart printout of the data transmitted, such as that pictured in FIGS. 8A and 8B. The chart printout device should be capable of simultaneously plotting two waveforms, one for the fetal heart rate data, and a second for the uterine contraction data.

The chart for plotting fetal heart rate information should have a vertical scale (chart width) of around 9 cm, a heart rate scale of approximately 30 bpm/cm (bpm=beats per minute), a range of at least 0-100 mm Hg, and a resolution of about 30-240 bpm.

The chart for plotting uterine activity information should have a vertical scale (chart width) around 4 cm, a pressure scale of approximately 25 mm Hg/cm, and a range of about 0-100 mm Hg.

The chart printout device should also have the capability of recording at different chart speeds, preferably having a slow chart speed of about 1 cm/min and a fast chart speed of about 3 cm/min. The accuracy of the chart printout device should be in the range of ±1%.

The preferred embodiment of the invention would typically be used in a manner as illustrated in FIG. 9. All of the set up information, (e.g. patient code, modem phone numbers, unit number, and session length), should be entered into memory 13 of FIG. 1 of the apparatus before it is given to the patient for use. This would be accomplished through the set up instructions as illustrated in FIG. 4 and described above.

As depicted in FIG. 9, the portable monitoring apparatus 25 should be compact and light enough to be moved easily by the user. First, apparatus 25 must be connected to a power source (a regular residential outlet) via power cable 29. Next, the telephone cable 27 should be used to connect the apparatus to a phone outlet. The event marker 47 must also be connected to apparatus 25, so that the user can hold the event marker during sampling to mark contractions or fetal movement as directed by the physician.

Ultrasound transducer should be connected to apparatus 25 at connector 39, and the pressure transducer or strain gage 15 should be connected to the apparatus at 41. Earphones 8 should also be connected to the apparatus at 37. All connections should be long enough to allow the patient user to relax in a comfortable position during the testing procedure, but not so long that they interfere with proper operation of the device, or produce distortion.

The patient user should be seated or reclining in a comfortable position, and she should put belt 23, which will be used to hold ultrasound transducer 1, around her body, below the waistline. She should then squeeze a thin layer of ultrasound gel, which acts as a conductor, around the inside edge of ultrasound transducer 1.

She should then put on earphones 8, and place ultrasound transducer 1 on her abdomen below the waistline, press down on it, and listen for the fetal heartbeat while looking at user display 19. The volume of earphones 8 can be adjusted with volume button 35. Numbers between 110-180 (an average range for fetal heart rate) should appear on user display 19. The mother should then continue listening to the heart beat with the headphones to find the optimum position where the signal is strongest, and secure ultrasound transducer 1 in that location with belt 23.

The mother should then place the second belt 21 around her body above first belt 23, and place the pressure transducer or strain gage 15 under second belt 21 to secure it in place. A pressure reading should appear on user display 19. Send button 33 should be pushed to clear this arbitrary pressure reading resulting from the pressure of belt 21.

The transducers are now properly connected to begin sampling data. The mother should press start button 31 to begin collecting data. When the sampling period is over, a message will appear on user display 19 indicating that all data has been collected. At this point, the mother can remove the belts and the transducers.

When the user is ready to transmit the data, she should push send button 45. At this point the apparatus will establish a connection via modem 14 to the remote monitoring station, and transmit the data telephonically. If an error results during transmission of data or if there is a problem establishing communications with the remote monitoring station, an error message will appear on user display 19. If this occurs, phone line connection 27 should be checked. If the data is successfully transmitted, user display 19 will display an appropriate message that transmission is finished and that power may now be shut off.

The remote monitoring station should be capable of displaying the transmitted data, complete with all identifying information, so that it can be used by the physician to make a diagnosis of the maternal and fetal conditions.

The following example is illustrative of preferred embodiments of methods of using the inventive device and is not to be construed as limiting the invention thereto.

EXAMPLE

A three part clinical study using the inventive apparatus was conducted by several obstetricians and hospitals. A total of 106 recordings and transmissions were obtained from 53 women.

In the first stage of the study, 30 women attempted 38 recordings and transmissions using the apparatus from a simulated home setting in a physician's clinic. In the second stage, 7 patients performed 40 recordings and transmissions with the apparatus set up in their homes. In the third stage, 16 patients performed 28 recordings and transmissions from a simulated home setting in the hospital. The results of all three stages are shown in Table 1.

Overall, in all three stages, 91.5% of the transmissions were successful, with 96.5% of the successful transmissions considered clearly adequate for interpretation based on the clarity of the signals and lack of background noise. It should be noted that these studies did not focus on differences in gestational age of the patients attempting the recordings and transmissions.

The average time required to teach the patients how to operate the apparatus was 10 minutes, while the average time required to train a nurse to staff the receiving station was 5 minutes.

A recording and transmission was considered a failure if the data was not successfully recorded or received by the receiving station. In three out of the nine cases that were considered recording and transmission failures, the incidence of the failure was due to outdated phone or electrical outlets at either the transmission or receiving ends. By ordering a computer phone line for the receiving end, and having the necessary phone or electrical adapters for the transmitting end, these failures were eliminated. There was one machine failure which was due to a loose wire in the transmission mechanism, which the monitor detected. The patient was notified by the apparatus that the data could not be transmitted.

Five of the nine failures were due to trouble tracking the fetus, but in two cases, at a later attempt, because the fetus was in a different position, the recordings were successful. In the third case, the fetus wa too active to track at the time of the attempt, and the patient refused a second attempt. In the fourth case, the patient was only in her 18th week of gestation and the fetus heart rate could not be located. In the fifth failure, the mother was obese and the recording was aborted due to weak signals.

Based upon the results a patient can successfully operate the apparatus at home, after minimal instructions. Furthermore, the quality and readability of the data transmitted over the phone was comparable to the data received on a conventional non-stress-testing machine at a hospital.

TABLE 1

|  | SIMULATED HOME SETTING (STAGES 1 & 3) | ACTUAL HOME SETTING (STAGE 2) | TOTAL |
|---|---|---|---|
| NO. OF SUBJECTS | 46 | 7 | 53 |
| TRANSMISSION ATTEMPTS | 66 | 40 | 106 |
| SUCCESSFUL TRANSMISSIONS | 58 (87.8%) | 39 (97.5%) | 97 (91.5%) |
| INTERPRETABLE NON-STRESS TEST | 56 (96.5%) | 38 (97.4%) | 94 (97%) |

The invention being thus described, it will be obvious that the same may be varied in many ways. Such variations are not to be regarded as a departure from the spirit and scope of the invention and all such modifications are intended to be included within the scope of the following claims.

What is claimed is:

1. Portable testing apparatus for non-invasive simultaneous self-testing of fetal and maternal signals, which comprises:
   a) first receiver means for receiving ultrasonic fetal signals;
   b) second receiver means for receiving maternal signals;
   c) signal processing means including a logarithmic amplification mean for amplifying the detected fetal heart signal;
   d) first communication means extending between said signal processing means and said first and second receiver means; and
   e) data output means connected to said signal processing means for simultaneous plural signal output.

2. The apparatus of claim 1 in which said data output means is also connected to a communication linking means.

3. The apparatus of claim 1 wherein said logarithmic amplification means has an input range of at least about −70 dbm to about +10 dbm and a low level gain of at least about 30 db.

4. The apparatus of claim 1 wherein said logarithmic amplification means has an input range of about −50 dbm to about +10 dbm and a low level gain of about 30 db to about 85 db.

5. The apparatus of claim 1 wherein said logarithmic amplification means has an input range of about −30 dbm to about +10 dbm and a low level gain of about 30 db to about 55 db.

6. The apparatus of claim 1 wherein said signal processing means includes filtering means for filtering the fetal heart signal.

7. The apparatus of claim 1 wherein said logarithmic amplification means has an input range of at least about −70 dbm to about +10 dbm.

8. The apparatus of claim 1 wherein said logarithmic amplification means has a low level gain of about 30 db.

9. The apparatus of claim 1 wherein said logarithmic amplification means has an input range of about −30 dbm to about +10 dbm.

10. Portable testing apparatus for non-invasive simultaneous self testing of fetal and maternal signals which comprises:
    a) ultrasonic means connected to said device for detecting a fetal heart rate;
    b) detection means connected to said device for detecting a maternal input signal;
    c) signal processing means for simultaneously processing fetal heart rate and maternal input signals, said signal processing means including a logarithmic amplification means for amplifying the detected fetal heart signal; and
    d) communication linking means for the simultaneous transmission of fetal heart rate and maternal input data to a remote output device.

11. The apparatus of claim 10 wherein said logarithmic amplification means has an input range of at least about −70 dbm to about +10 dbm and a low level gain of at least about 30 db.

12. The apparatus of claim 10 wherein said logarithmic amplification means has an input range of about −50 dbm to about +10 dbm and a low level gain of about 30 db to about 85 db.

13. The apparatus of claim 10 wherein said logarithmic amplification means has an input range of about −30 dbm to about +10 dbm and a low level gain of about 30 db to about 55 db.

14. The apparatus of claim 10 wherein said signal processing means includes filtering means for filtering the fetal heart signal.

15. The apparatus of claim 10 wherein said logarithmic amplification means has an input range of about −50 dbm to about 10 dbm.

16. The apparatus of claim 10 wherein said logarithmic amplification means has a low level gain of at least about 30 db.

17. The apparatus of claim 10 wherein said logarithmic amplification means has an input range of at least about −70 dbm to about +10 dbm.

18. Portable testing apparatus for non-invasive simultaneous self-testing of fetal and maternal signals, which comprises:
    a) ultrasonic means connected to said device for detecting fetal heart rate;
    b) detection means connected to said device for detecting a maternal input signal;
    c) signal processing means for simultaneously processing fetal heart rate and maternal input signals, said signal processing means including a logarithmic amplification means for amplifying the detected fetal heart signal;
    d) communication linking means for the simultaneous transmission of fetal heart rate and maternal input data to a remote output device; and
    e) an output device for reading transmitted data.

19. The apparatus of claim 18 wherein said logarithmic amplification means has an input range of at least about −70 dbm to about +10 dbm and a low level gain of at least about 30 db.

20. The apparatus of claim 18 wherein said logarithmic amplification means has an input range of about −50 dbm to about 10 dbm and a low level gain of about 30 db to about 85 db.

21. The apparatus of claim 18 wherein said logarithmic amplification means has an input range of about −30 dbm to about +10 dbm and a low level gain of about 30 db to about 55 db.

22. The apparatus of claim 18 wherein said signal processing means includes filtering means for filtering the fetal heart signal.

23. The apparatus of claim 18 wherein said logarithmic amplification means has an input range of about −50 dbm to about 30 dbm.

24. The apparatus of claim 18 wherein said logarithmic amplification means has a low level gain of at least about 30 db.

25. The apparatus of claim 18 wherein said logarithmic amplification means has an input range of at least about −70 dbm to about +10 dbm.

26. A method of determining the condition of a fetus in a maternal uterus, which comprises:
    a) measuring a pressure in the uterus as a function of time;
    b) measuring a heart rate of the fetus using an ultrasonic detection means;
    c) logarithmically amplifying the detected fetal heart rate;
    d) simultaneously recording the uterine pressure measurements and the fetal heart rate;
    e) simultaneously transmitting said pressure measurements and fetal heart rate by communication linking means to a remote location.

* * * * *

UNITED STATES PATENT AND TRADEMARK OFFICE
CERTIFICATE OF CORRECTION

PATENT NO. : 5,265,613
DATED : November 30, 1993
INVENTOR(S) : FELDMAN ET AL

It is certified that error appears in the above-identified patent and that said Letters Patent is hereby corrected as shown below:

Claim 1, column 17, line 9, replace "mean" with --means--.

Claim 23, column 18, line 48, replace " 30 dbm" with

--10 dbm--.

Signed and Sealed this

Twenty-sixth Day of April, 1994

Attest:

BRUCE LEHMAN

*Attesting Officer*   *Commissioner of Patents and Trademarks*